United States Patent [19]

Remy

[11] 4,132,796
[45] * Jan. 2, 1979

[54] ANTIPSYCHOTIC 3-TRIFLUOROMETHYLSULFINYL ANALOGS OF CYPROHEPTADINE

[75] Inventor: David C. Remy, North Wales, Pa.

[73] Assignee: Merck & Co., Inc., Rahway, N.J.

[*] Notice: The portion of the term of this patent subsequent to Jun. 21, 1994, has been disclaimed.

[21] Appl. No.: 856,556

[22] Filed: Dec. 1, 1977

[51] Int. Cl.$^2$ ............... C07D 211/24; A61K 31/445
[52] U.S. Cl. .................................... 424/267; 546/204
[58] Field of Search .................... 260/293.62; 424/267

[56] References Cited

U.S. PATENT DOCUMENTS

| 3,014,911 | 12/1961 | Engelhardt | 260/293.62 |
| 3,862,156 | 1/1975 | Bourquin et al. | 260/293.57 |
| 4,031,222 | 6/1977 | Remy | 260/293.62 |

OTHER PUBLICATIONS

Migrdichian, V., Organic Synthesis, vol. 1, Reinhold Pub. Corp., NY, 1957 pp. 465–467.

Yagupolskii, L. et al., Zm. Obshch. Khim. 35(2), 377–387 (1965) [Chemical Abstracts 62:14551a (1965)].
Orda, V. et al., Dopovidi Akad. Nauk. UKR RSR 1965(3), 345–348 [Chemical Abstracts, 63:1684g (1965)].
Syrova, G. et al., Zh. Org. Khim. 1970, 6(11), 2285–2289 [Chemical Abstracts, 74:52873j (1971)].

*Primary Examiner*—Henry R. Jiles
*Assistant Examiner*—Richard A. Schwartz
*Attorney, Agent, or Firm*—William H. Nicholson; Mario A. Monaco

[57] ABSTRACT

Cyproheptadine derivatives substituted with a trifluoromethylsulfinyl group in one of the benzo rings and having an alkyl group, either unsubstituted or substituted with a hydroxy or cycloalkyl group, on the piperidine nitrogen are potent antipsychotic agents, with a low propensity to induce extrapyramidal side effects that are experienced with most major tranquilizers. The novel compounds are generally prepared by treatment of the intermediate 5-carbinol with a dehydrating reagent, or by alkylation of the piperidine nitrogen with the appropriate alkyl or substituted alkyl group.

8 Claims, No Drawings

ANTIPSYCHOTIC 3-TRIFLUOROMETHYLSULFINYL ANALOGS OF CYPROHEPTADINE

BACKGROUND OF THE INVENTION

Traditionally, in the dibenzocycloheptene series of compounds, those with a piperidinylidene group in the 5-position have been considered to be without notable antipsychotic action. Recently, however, 3-cyanocyproheptadine, 3-trifluoromethylthiocyproheptadine, 3-trifluoromethylsulfonylcyproheptadine and analogs of the latter two compounds having a cycloalkyl-alkyl or hydroxy alkyl group on the piperidine nitrogen have been described as having antipsychotic activity.

It has now been found that trifluoromethyl-sulfinyl derivatives of cyproheptadine and analogs carrying a hydroxyalkyl or cycloalkylalkyl group on the piperidine nitrogen are also potent antipsychotic agents, with a low propensity to induce extrapyramidal side effects.

It is thus an object of the present invention to provide novel compounds which are potent antipsychotic agents.

It is a further object of this invention to provide novel processes for the preparation of the novel compounds.

Another object of the invention is to provide novel pharmaceutical compositions comprising the novel compounds as active ingredient.

Another object of the invention is to provide a novel method of treating psychoses by administration of the novel antipsychotic compounds or pharmaceutical compositions thereof to a patient.

DETAILED DESCRIPTION OF THE INVENTION

The novel compounds of this invention have the following structural formula:

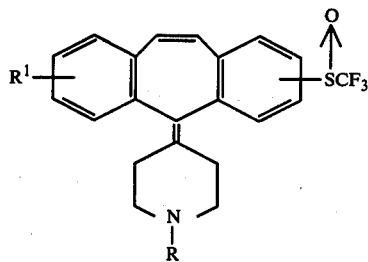

or pharmaceutically acceptable salt thereof, wherein: R represents
(1) lower alkyl of 1-3 carbons, especially —CH$_3$, (2)

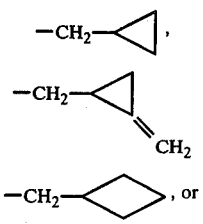

(3)

(4)

(5) —CH$_2$CH$_2$OH; and
R$^1$ represents hydrogen, lower alkyl of 1-3 carbon atoms, or fluoro.

A preferred embodiment of the novel compounds is that wherein R$^1$ is hydrogen.

A still more preferred embodiment is that wherein R$^1$ is hydrogen, the

is in the 3-position, and R is

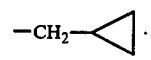

The introduction of nuclear substituents into the 3-position of cyproheptadine and its N-alkyl analogs and derivatives results in the introduction of atropisomerism into the series. Thus, a 3-substituted cyproheptadine derivative, when prepared, exists as an enantiomeric, or (d,l), pair of isomers. A sulfoxide also exists as an enantiomeric, or (d,l), pair of isomers. Accordingly, each of the novel products of this invention exists as two diastereomeric pairs by virtue of these chiralities. Each product is, therefore, amenable to separation by fractional crystallization into its constituent diastereomers, each of which in turn can be resolved into its enantiomeric constituents.

In the case wherein R is

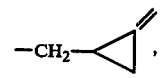

there is an asymmetric carbon atom in the cyclopropyl ring, and, therefore, the product exists as eight stereoisomers.

The pharmaceutically acceptable salts of the novel compounds of this invention are acid addition salts formed from a novel compound and an organic or inorganic acid recognized by the art as providing a pharmaceutically acceptable acid addition salt, such as hydrochloride, hydrobromide, dihydrogen phosphate, sulfate, citrate, pamoate, pyruvate, napsylate, isethionate, maleate, fumarate, or the like.

These salts are readily prepared by mixing solutions of equimolecular amounts of the free base compound and the desired acid in suitable solvents such as water, alcohols, ether or chloroform, followed by recovery of the product by collecting the precipitated salt or evaporation of the solvent.

A novel process for obtaining the novel compounds of this invention is shown schematically as follows:

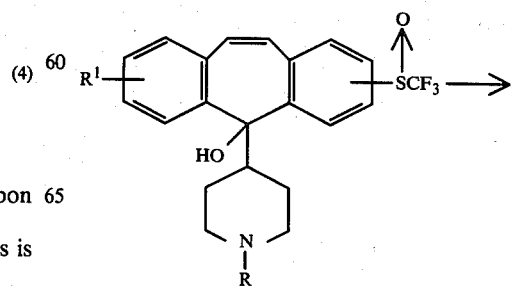

-continued

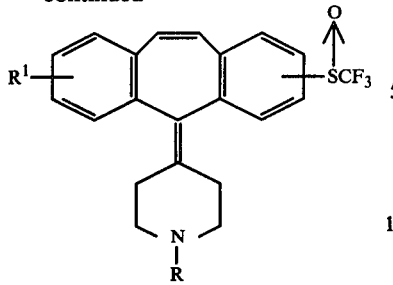

This process comprises heating the starting material with a dehydrating agent such as hydrochloric acid or a mixture of trifluoroacetic acid and trifluoroacetic anhydride, preferably the latter at about 50° C. to reflux temperature for 10 to about 100 hours.

Another process for obtaining the novel compounds of this invention comprises alkylation of the piperidine nitrogen and is shown as follows:

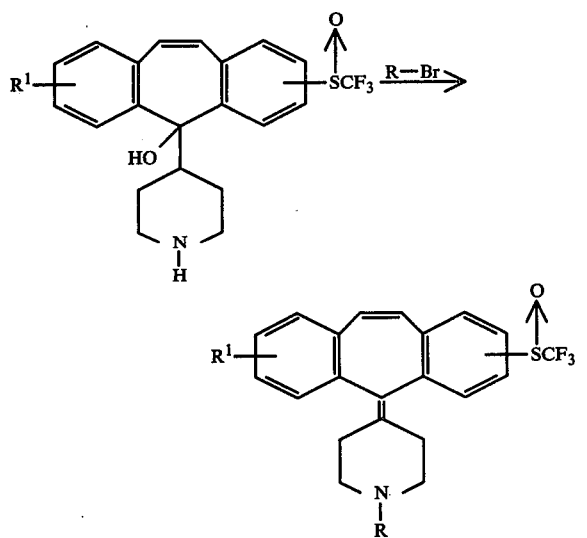

The process comprises treating the secondary amine starting material with an excess of the reagent R-Br in an inert organic solvent such as a lower alkanol, preferably ethanol, in the presence of an acid acceptor such as a basic resin, pyridine, quinoline, or a solid alkali metal bicarbonate such as sodium bicarbonate, and heating the mixture at 50° C. to reflux temperature from 12 to about 48 hours.

In the case wherein R is —CH$_2$CH$_2$OH, the preferred reagent to employ is ethylene oxide. The process is conducted by treating the secondary amine starting material with an excess of ethylene oxide in a lower alkanol such as methanol or ethanol at about −80° C. and permitting the reaction mixture to warm spontaneously to room temperature and maintaining at room temperature about 10 to 24 hours.

Following any of the foregoing processes, the product isolated may be found to be enriched in one or the other of the diastereomers. The product may be completely separated into its diastereomeric pairs by fractional crystallization each of which may be resolved.

On the other hand, a product that is obtained enriched in one of the diastereomeric pairs can be obtained in a 1:1 diastereomeric pair ratio by heating a solution of the product in an inert solvent. It is convenient to reflux a toluene solution of the product for about 10–30 hours.

The novel method of treatment of this invention comprises the administration of one of the novel compounds to a psychotic patient. The route of administration can be oral, rectal, intravenous, intramuscular, or subcutaneous. Doses of 0.1 to 20 mg./kg./day and preferably of 0.5 to 10 mg./kg./day of active ingredient are generally adequate, and if preferred it can be administered in divided doses given two to four times daily.

It is to be noted that the precise unit dosage form and dosage level depend upon the requirements of the individual being treated and, consequently, are left to the discretion of the therapist.

Pharmaceutical compositions comprising a novel compound as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and subcutaneous use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 to 400 mg., and preferably from 5 to 250 mg.

EXAMPLE 1

1-Cyclopropylmethyl-4-(3-trifluoromethylsulfinyl-5H-dibenzo[a,d]cyclohepten-5-ylidene)piperidine Step A: Preparation of 3-trifluoromethylthio-5H-dibenzo[a,d]cyclohepten-5-one A mixture of 42.56 g. of bis(trifluoromethylthio)mercury, 17.27 g. of 3-bromo-5H-dibenzo[a,d]cyclohepten-5-one, 28 g. of electrolytic copper dust, 98 ml. of quinoline and 84 ml. of pyridine is stirred and heated from 100° C. to 195° C. and held at 195° C. for 18 hours. The mixture is shaken with 400 ml. of 6N hydrochloric acid and 400 ml. benzene. The organic phase is washed with 5 × 300 ml. of 3 N hydrochloric acid and 5 × 300 ml. of water, dried over magnesium sulfate, filtered and concentrated to dryness. The crystalline residue is recrystallized from 100 ml. of methanol to give 14.83 g. (78%) of 3-trifluoromethylthio-5H-dibenzo[a,d]cyclohepten-5-one, m.p. 87–88° C. Sublimation at 100° C. (0.5 mm Hg) provides material with m.p. 94.5–95° C.

Following the procedure of Example 1, Step A, but substituting for the starting material used therein an equimolar amount of 3-bromo-7-methyl-5H-dibenzo[a,d]cyclohepten-5-one and 3-bromo-7-fluoro-5H-dibenzo[a,d]cyclohepten-5-one, there are produced, respectively, 3-trifluoromethylthio-7-methyl)and 7-fluoro)-5H-dibenzo[a,d]cyclohepten-5-one.

Step B: Preparation of 1-cyclopropylmethyl-4-(3-trifluoromethylthio-5-hydroxy-5H-dibenzo[a,d]cyclohepten-5-yl)piperidine To an ice-cooled solution of 10.0 g. (0.0326 mol) of 3-trifluoromethylthio-5H-dibenzo[a,d]cyclohepten-5-one in 60 ml. of dry tetrahydrofuran is added dropwise 29 ml. of 1.14 M 1-cyclopropylmethyl-4-piperidylmagnesium chloride in tetrahydrofuran. The solution is stirred for two hours while being allowed to warm to room temperature, and then the tetrahydrofuran is removed on a rotary evaporator. The red, oily residue that remains is dissolved in benzene and water is added dropwise until a clear benzene supernatant and a gelatinous aqueous phase is obtained. The benzene phase is decanted and the gelatinous aqueous phase is extracted with two 100 ml. portions of hot benzene. The combined benzene extracts are washed with four 150 ml. portions of water, dried over magnesium sulfate, filtered, and the benzene is removed on a rotary evaporator. The remaining residue is placed on a silica gel column packed in chloroform. The column is eluted with chloroform which causes a by-product of the reaction, 3-trifluoromethylthio-5H-dibenzo[a,d]cyclohepten-5-ol, to be eluted. (This by-product may be oxidized to provide the starting material, 3-trifluoromethylthio-5H-dibenzo[a,d]cyclohepten-5-one). When all of the by-product has been eluted, the column is eluted with 2% methanol in chloroform. The eluate is concentrated to give 7.0 g. of an oil which is mainly 1-cyclopropylmethyl-4-(3-trifluoromethylthio-5-hydroxy-5H-dibenzo[a,d]cyclohepten-5-yl)piperidine.

Following the procedure of Example 1, Step B, but substituting for the 3-trifluoromethylthio-5H-dibenzo[a,d]cyclohepten-5-one and 1-cyclopropylmethyl-4-piperidylmagnesium chloride used therein, corresponding amounts, on a molecular basis, of the $R^1$-3-trifluoromethylthio-5H-dibenzo[a,d]cyclohepten-5-ones and 1-R-4-piperidylmagnesium chloride, there are produced the 1-R-4-($R^1$-3-trifluoromethylthio-5-hydroxy-5H-dibenzo[a,d]-cyclohepten-5-yl)piperidines described in Table I, in accordance with the following reaction scheme:

TABLE I

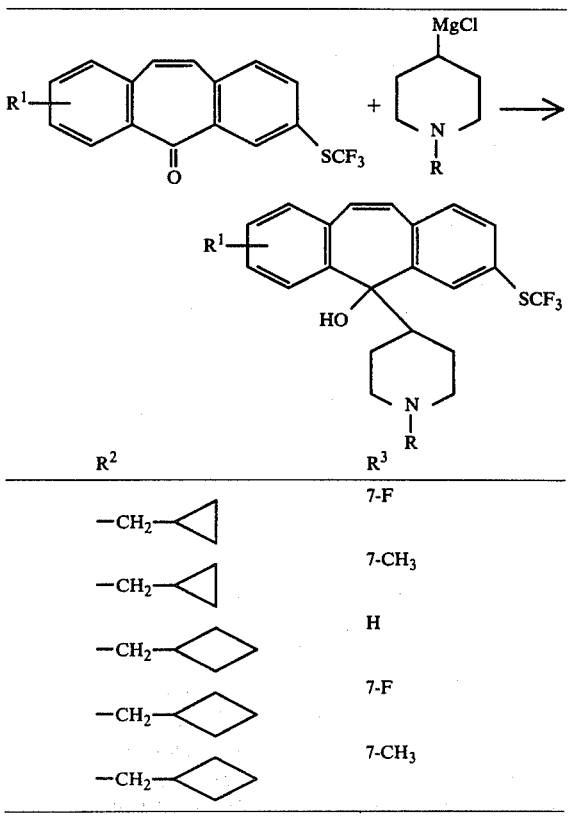

| $R^2$ | $R^3$ | |
|---|---|---|
| —CH$_2$—△ | | 7-F |
| —CH$_2$—△ | | 7-CH$_3$ |
| —CH$_2$—◇ | | H |
| —CH$_2$—◇ | | 7-F |
| —CH$_2$—◇ | | 7-CH$_3$ |

Step C: Preparation of (±)-cyclopropylmethyl-4-(3-trifluoromethylsulfinyl-5H-dibenzo[a,d]cyclohepten-5-ylidene)piperidine A solution of 27.84 g. of the oil from Step B, consisting mainly of 1-cyclopropylmethyl-4-(3-trifluoromethylthio-5-hydroxy-5H-dibenzo[a,d]cyclohepten-5-yl) piperidine, 280 ml. of glacial acetic acid, and 37 ml. of 30% hydrogen peroxide is stirred at room temperature for 69 hours. The solution is poured into one liter of water and potassium carbonate is added until the mixture is basic to litmus paper. The mixture is extracted with three 250 ml. portions of chloroform. The combined chloroform extracts are washed with three 500 ml. portions of water, and, after drying over magnesium sulfate, the mixture is filtered and the chloroform is removed on a rotary evaporator. The residue is dissolved in 400 ml. of dioxane, stirred, and sulfur dioxide gas is bubbled into the solution for 15 minutes. The solution, which becomes warm during this time, is allowed to stir an additional 10-15 minutes. The dioxane is then removed by evaporation. The residue is dissolved in 100 ml. of trifluoroacetic acid and 100 ml. of trifluoroacetic anhydride, stirred, and is refluxed for 19 hours. The solution is evaporated to dryness in vacuo, and the residue is made basic with saturated sodium bicarbonate solution. The oil that precipitates is extracted into ether, and the ether phase is washed with water, dried over magnesium sulfate, filtered, and the ether removed on a rotary evaporator. The residue, which crystallizes rapidly, is triturated with acetonitrile and collected by filtration to give 6.73 g. of 1-cyclopropylmethyl-4-(3-trifluoromethylsulfinyl-5H-dibenzo[a,d]cyclohepten-5-ylidene)piperidine that contains a very small amount of two impurities, namely (±)-1-cyclopropylmethyl-4-(3-trifluoromethylthio-5H-dibenzo[a,d]cyclohepten-5-ylidene) piperidine and (±)-1-cyclopropylmethyl-4-(3-trifluoromethylsulfonyl)-5H-dibenzo[a,d]cyclohepten-5-ylidene) piperidine. These two impurities are removed from the desired material by chromatography on alumina using toluene as a developing agent. The desired trifluoromethyl-sulfinyl compound travels at a slower rate than do the two impurities. Thus, after the appropriate fractions are combined and concentrated to dryness, there is obtained 3.89 g. of crystalline product. Recrystallization of this material from acetonitrile gives 1-cyclopropylmethyl-4-(3-trifluoromethylsulfinyl-5H-dibenzo[a,d]cyclohepten-5-ylidene)piperidine, m.p. 146-148° C. An examination of the $^{19}F$ NMR spectrum of this material shows two peaks indicating the presence of both diastereomers and in an approximate ratio of 9:1.

A solution of 1.1 g. of the above material, having a diastereomer ratio of 9:1, dissolved in 50 ml. of toluene is stirred and refluxed for 24 hours. The solution is concentrated to dryness. The crystalline residue is dissolved in ether, filtered, and the ether is removed by evaporation. The product is dried to give 1-cyclopropylmethyl-4-(3-trifluoromethylsulfinyl-5H-dibenzo[a,d]cyclohepten-5-ylidene)piperidine, m.p. starts to soften at 110° and there is a clear melt by 130° C. An examination of the $^{19}F$ NMR spectrum of this material shows two peaks indicating the presence of both diastereomers and in an approximate ratio of 1:1.

Following the procedure of Example 1, Step C, but substituting for the 1-cyclopropylmethyl-4-(3-trifluoromethylthio-5-hydroxy-5H-dibenzo[a,d]cyclohepten-5-yl)piperidine used therein, an equimolecular amount of the 1-R-4-(R$^1$-3-trifluoromethylthio-5-hydroxy-5H-dibenzo[a,d]cyclohepten-5-yl)piperidine described in Table II, there are produced 1-R-4-(R$^1$-3-trifluoromethylsulfinyl-5H-dibenzo[a,d]cyclohepten-5-ylidene)piperidines, also described in Table II in accordance with the following reaction scheme:

TABLE II

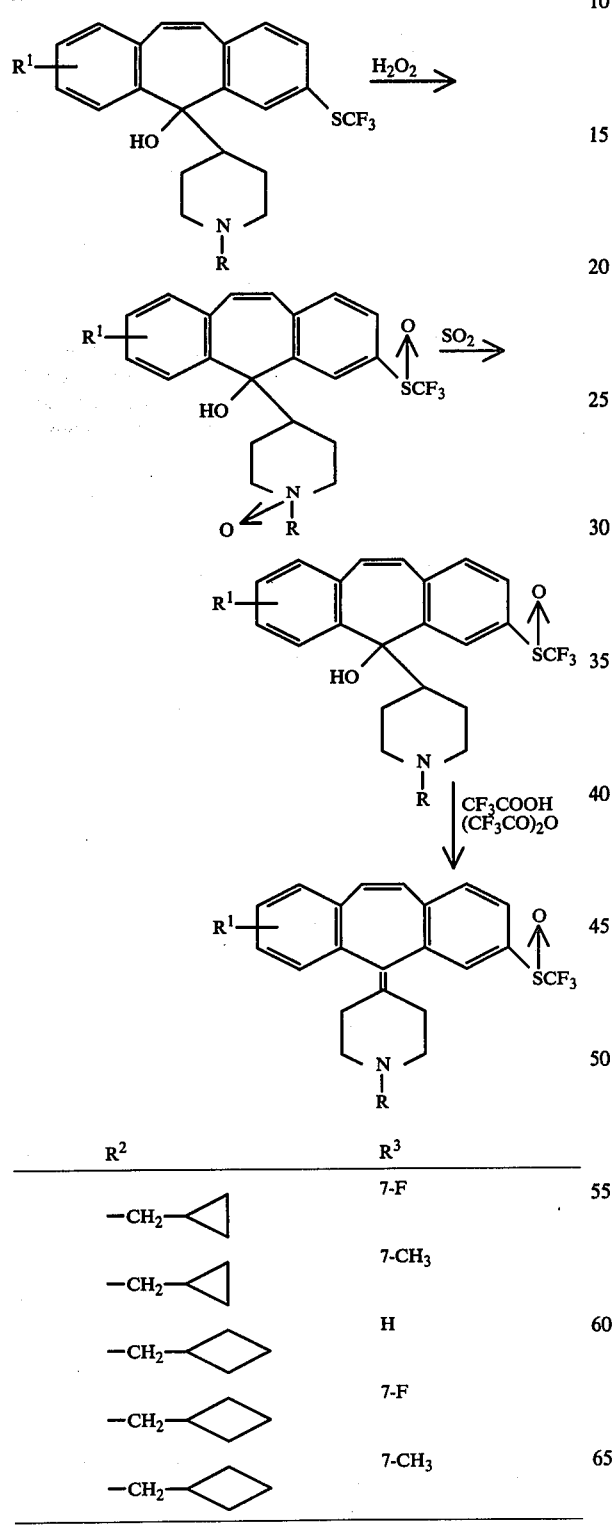

| R$^2$ | R$^3$ |
|---|---|
| —CH$_2$—△ | 7-F |
| —CH$_2$—△ | 7-CH$_3$ |
| —CH$_2$—◇ | H |
| —CH$_2$—◇ | 7-F |
| —CH$_2$—◯ | 7-CH$_3$ |

EXAMPLE 2

1-Methylenecyclopropylmethyl-4-(3-trifluoromethylsulfinyl-5H-dibenzo[a,d]cyclohepten-5-ylidene)piperidine Step A: Preparation of 4-(3-trifluoromethylsulfinyl-5H-dibenzo[a,d]cyclohepten-5-ylidene)piperidine A solution of 4.32 g. of 1-cyclopropylmethyl-4-(3-trifluoromethylsulfinyl-5H-dibenzo[a,d]cyclohepten-5-ylidene)piperidine in 35 ml. of benzene is added dropwise over 45 minutes to a stirred solution of 1.3 g. of cyanogen bromide in 35 ml. of benzene. After stirring at room temperature overnight the solution is evaporated to dryness and co-evaporated with acetonitrile.

To the oily residue is added 100 ml. of acetic acid, 12 ml. of concentrated hydrochloric acid, and 50 ml. of water. This mixture is refluxed for 16 hours. The mixture is concentrated to dryness in vacuo. The residue is dissolved in chloroform and made basic by addition of sodium bicarbonate solution. The aqueous phase is extracted well with chloroform and the combined organic layers are washed with water, dried and filtered. The filtrate is concentrated to dryness in vacuo to give 4-(3-trifluoromethylsulfinyl-5H-dibenzo[a,d]cyclohepten-5-ylidene)piperidine.

Step B: Preparation of 1-methylenecyclopropylmethyl-4-(3-trifluoromethylsulfinyl-5H-dibenzo[a,d]cyclohepten-5-ylidene)piperidine A mixture of 2 g. of the product from Step A, 0.5 g. of sodium bicarbonate and 0.778 g. of methylenecyclopropylmethylbromide in 60 ml. of absolute ethanol is refluxed overnight. An additional amount of 0.132 g. of the bromide is added and refluxing is continued for 6 more hours when another 0.132 g. of bromide is added followed by refluxing overnight. The cooled mixture is filtered and the filtrate is concentrated to dryness in vacuo. The residue is partitioned between water and chloroform. The separated water phase is extracted again with chloroform. The combined chloroform extracts are washed with water, dried over magnesium sulfate and concentrated to dryness. Recrystallization of the residue from acetonitrile gives 1-methylenecyclopropylmethyl-4-(3-trifluoromethylsulfinyl-5H-dibenzo[a,d]cyclohepten-5-ylidene)piperidine.

Employing the procedure substantially as described in Example 2, but substituting for the 1-cyclopropylmethyl-4-(3-trifluoromethylsulfinyl-5H-dibenzo[a,d]-cyclohepten-5-ylidene)piperidine used in Step A and the methylenecyclopropylmethyl bromide used in Step B, corresponding amounts, respectively, of the 1-cyclopropylmethyl-4-(R$^1$-3-trifluoromethylsulfinyl-5H-dibenzo[a,d]cyclohepten-5-ylidene)piperidines and the R-Br compounds described in Table III, there are produced the 1-R-4-(R$^1$-trifluoromethylsulfinyl-5H-dibenzo[a,d]cyclohepten-5-ylidene)piperidine compounds also described in Table III in accordance with the following reaction scheme:

TABLE III

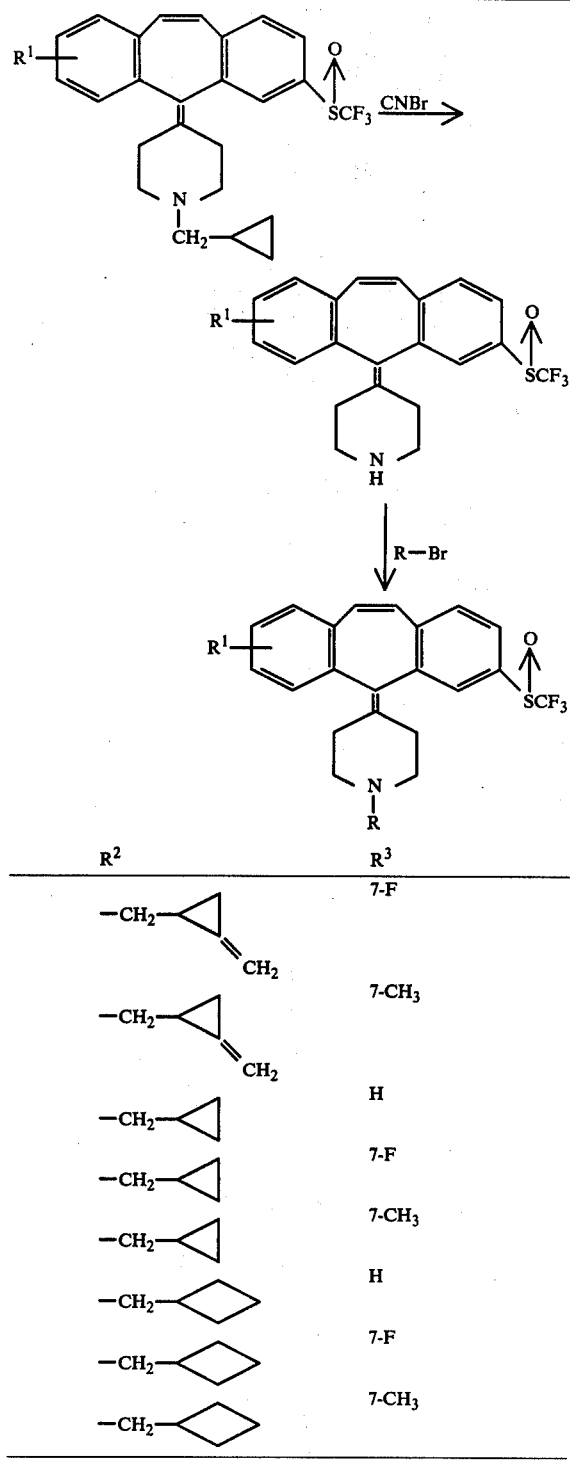

| R² | R³ |
|---|---|
| —CH₂—◁=CH₂ | 7-F |
| —CH₂—◁=CH₂ | 7-CH₃ |
| —CH₂—◁ | H |
| —CH₂—◁ | 7-F |
| —CH₂—◁ | 7-CH₃ |
| —CH₂—◇ | H |
| —CH₂—◇ | 7-F |
| —CH₂—◇ | 7-CH₃ |

EXAMPLE 3

1-Hydroxyethyl-4-(3-trifluoromethylsulfinyl-5H-dibenzo[a,d]cyclohepten-5-ylidene)piperidine A solution of 0.244 g. of ethylene oxide in 30 ml. of methanol at dry-ice temperature is added to an ice cold solution of 2.25 g. of 4-(3-trifluoromethylsulfinyl-5H-dibenzo[a,d]cyclohepten-5-ylidene)piperidine in 15 ml. of chloroform and 75 ml. of methanol. The solution is stirred at ambient temperature overnight. A second quantity (0.25 g.) of ethylene oxide is added as before and the mixture is again stirred overnight. The mixture is concentrated to dryness and the residue is co-evaporated in vacuo several times with acetonitrile. The product is recrystallized several times from acetonitrile to give 1-hydroxyethyl-4-(3-trifluoromethylsulfinyl-5H-dibenzo[a,d]cyclohepten-5-ylidene)piperidine.

EXAMPLE 4

Pharmaceutical Compositions

A typical tablet containing 100 mg. of 1-cyclopropylmethyl-4-(3-trifluoromethylsulfinyl-5H-dibenzo[a,d]cyclohepten-5-ylidene)piperidine per tablet is prepared by mixing together with the active ingredient calcium phosphate, lactose and starch in the amounts shown in the table below. After these ingredients are thoroughly mixed, the appropriate amount of magnesium stearate is added and the dry mixture blended for an additional three minutes. This mixture is then compressed into tablets.

| Tablet Formula | |
|---|---|
| Ingredient | Mg. per Tablet |
| 1-cyclopropylmethyl-4-(3-trifluoromethylsulfinyl-5H-dibenzo[a,d]-cyclohepten-ylidene)piperidine | 100 mg. |
| Calcium phosphate | 52 mg. |
| Lactose | 60 mg. |
| Starch | 10 mg. |
| Magnesium stearate | 1 mg. |

Similarly prepared are tablets comprising as active ingredient any of the antipsychotic compounds described herein.

What is claimed is:

1. A compound of structural formula:

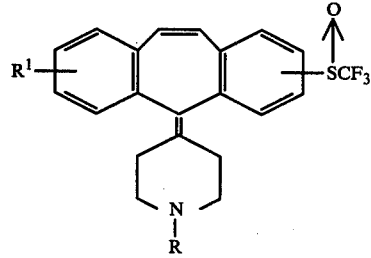

or a pharmaceutically acceptable salt thereof, wherein

R is (1) 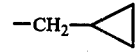

(2) 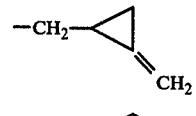

(3) 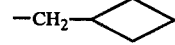

(4) —CH₂CH₂OH; and R¹ is hydrogen, C₁₋₃ alkyl or fluoro.

2. The compound of claim 1 of structural formula:

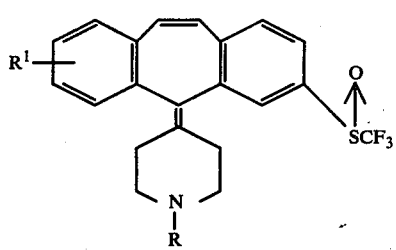

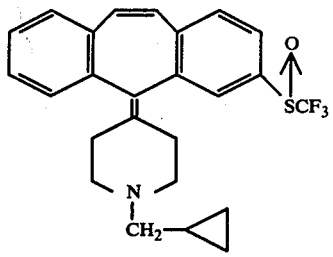

or pharmaceutically acceptable salt thereof.

3. The compound of claim 2 or pharmaceutically acceptable salt thereof wherein $R^1$ is hydrogen.

4. The compound of claim 3, which is 1-cyclopropyl-methyl-4-(3-trifluoromethylsulfinyl-5H-dibenzo[a,d]-cyclohepten-5-piperidine, or pharmaceutically acceptable salt thereof.

5. A pharmaceutical composition in unit dosage form for the treatment of psychoses comprising a pharmaceutically acceptable carrier and an effective antipsychotic amount of a compound of structural formula:

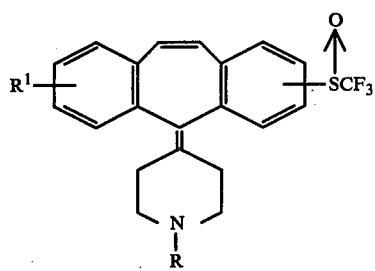

or a pharmaceutically acceptable salt thereof, wherein

R is —CH$_2$—◁ (1)

—CH$_2$—◁=CH$_2$ (2)

—CH$_2$—▱ , or (3)

(4) —CH$_2$CH$_2$OH; and $R^1$ is hydrogen, C$_{1-3}$ alkyl or fluoro.

6. The pharmaceutical composition of claim 5, wherein the compound is of structural formula:

or pharmaceutically acceptable salt thereof.

7. A method of treating psychoses which comprises the administration to a patient in need of such treatment an effective antipsychotic amount of a compound of structural formula:

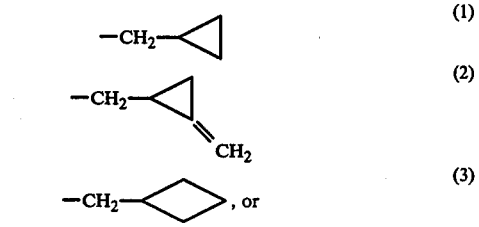

or pharmaceutically acceptable salt thereof, wherein

—CH$_2$—◁ (1)

—CH$_2$—◁=CH$_2$ (2)

—CH$_2$—▱ , or (3)

(4) —CH$_2$CH$_2$OH; and $R^1$ is hydrogen, C$_{1-3}$ alkyl or fluoro.

8. The method of claim 7 wherein the compound is of structural formula:

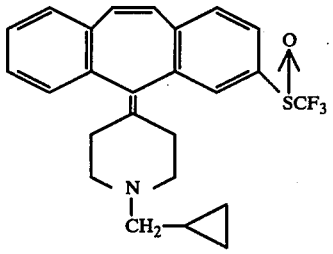

or pharmaceutically acceptable salt thereof.

* * * * *